US00PP19278P2

(12) United States Plant Patent
Pierce

(10) Patent No.: US PP19,278 P2
(45) Date of Patent: Sep. 30, 2008

(54) ***CALIBRACHOA* PLANT NAMED 'CAL PUR07'**

(50) Latin Name: ***Calibrachoa* sp.**
Varietal Denomination: Cal Pur07

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/827,217

(22) Filed: Jul. 11, 2007

(51) Int. Cl.
*A01H 5/00* (2006.01)

(52) U.S. Cl. ..... Plt./413
(58) Field of Classification Search ..... Plt./413
See application file for complete search history.

(56) References Cited

U.S. PATENT DOCUMENTS

PP14,703 P2 * 4/2004 Pierce ..... Plt./413
PP15,427 P2 * 12/2004 Pierce ..... Plt./413

OTHER PUBLICATIONS

UPOV ROM GTITM Computer Database GTI Jouve Retrieval Software Citation for 'cal Pur07'.*

* cited by examiner

*Primary Examiner*—Wendy C. Haas
(74) *Attorney, Agent, or Firm*—Jondle & Associates, P.C.

(57) ABSTRACT

A new *Calibrachoa* plant particularly distinguished by purple flowers, early and continuous flowering, dark green foliage, good vigor, semi-upright to later prostrate or trailing habit, is disclosed.

1 Drawing Sheet

Genus and species: *Calibrachoa* sp.
Variety denomination: 'Cal Pur07'.

BACKGROUND OF THE NEW PLANT

The present invention comprises a new and distinct cultivar of *Calibrachoa,* botanically known as *Calibrachoa* sp., and hereinafter referred to by the cultivar name 'Cal Pur07'. The new cultivar originated from a hybridization made in July 2003 in Gilroy, Calif. The female parent was the proprietary purple-flowered *Calibrachoa* plant '#33' (unpatented), while the male parent was the proprietary deep blue-flowered *Calibrachoa plant* '#30' (unpatented). The seeds produced by the hybridization were sown in January 2004 in Gilroy, Calif. A single plant selection was chosen for further evaluation and for asexual propagation in April 2004 in Gilroy, Calif.

The new cultivar was created in 2003 in Gilroy, Calif. and has been asexually reproduced repeatedly by vegetative cuttings and tissue culture in Gilroy, Calif., Andijk, The Netherlands and Hillscheid, Germany over a three-year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar were applied for in the European Union on Feb. 27, 2007 and in Switzerland on Oct. 30, 2006.

SUMMARY OF THE INVENTION

The following are the most outstanding and distinguishing characteristics of this new cultivar when grown under normal horticultural practices in Gilroy, Calif. and Hillscheid, Germany.

1. Purple flowers;
2. Narrow, dark green foliage;

3. Good vigor;
4. Semi-upright to later prostrate to trailing plant habit; and
5. An early and continuous flowering response.

DESCRIPTION OF PHOTOGRAPHS

This new *Calibrachoa* plant is illustrated by the accompanying photographs which show overall plant habit including blooms, buds, and foliage of the plant; the colors shown are as true as can be reasonably obtained by conventional photographic procedures. The photographs are of whole plants about 20-weeks old, grown in a greenhouse in Hillscheid, Germany. The potted plant photograph was taken in May. The basket plants were moved outside to grow in the summer and the photograph was taken in August.

DESCRIPTION OF THE NEW CULTIVAR

Figure 1:
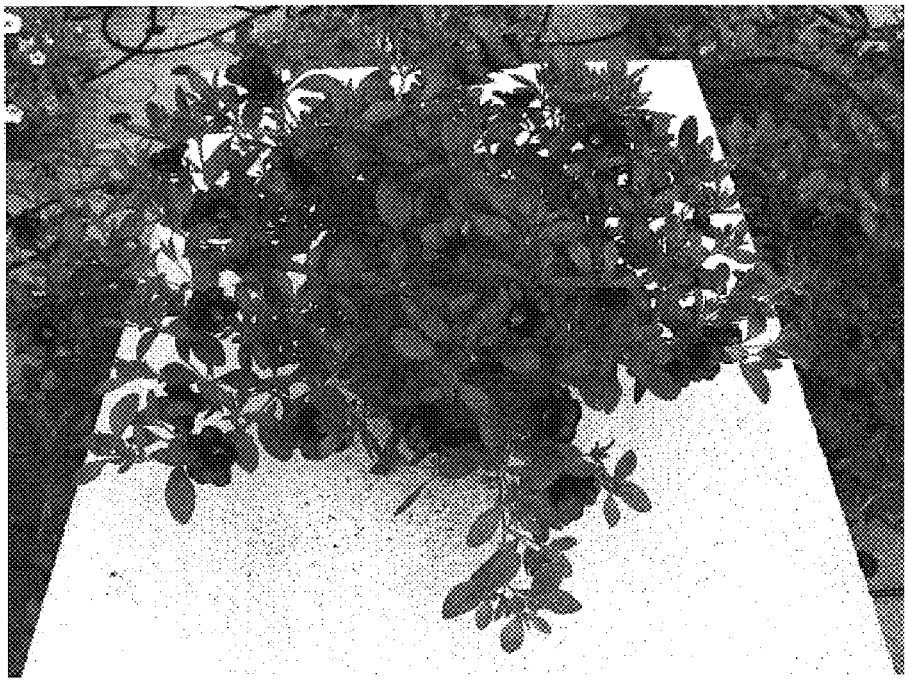
FIG. 1 shows a close-up of the mature flowers.
Figure 2:
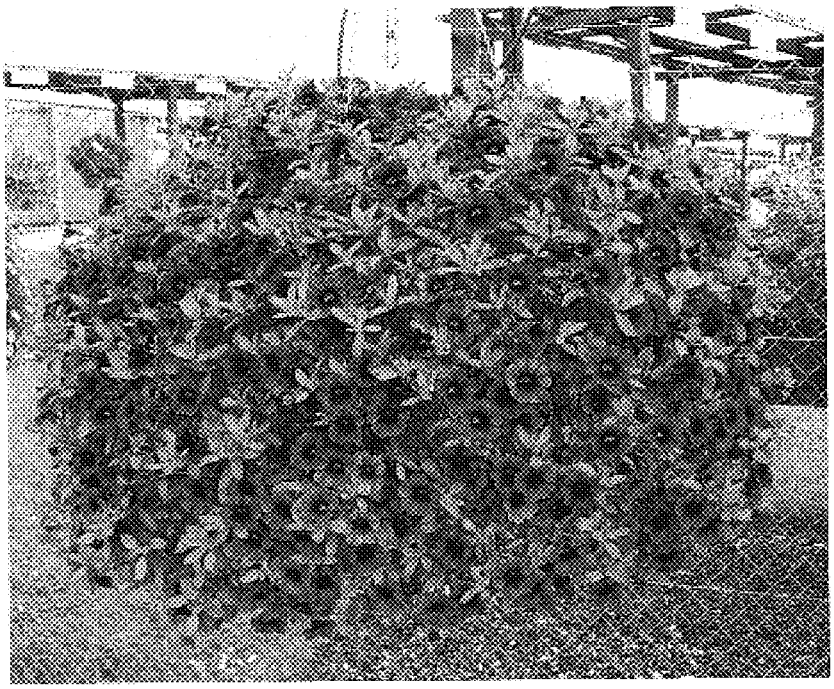
FIG. 2 shows the overall plant habit, including blooms, buds, and foliage.

The following detailed description sets forth the distinctive characteristics of 'Cal Pur07'. The data which define these characteristics were collected from asexual reproductions carried out in Gilroy, Calif. The plant history was taken on 16–20-week old plants grown in 6-inch pots in a greenhouse in the spring season in a trial setting. The plants had one plant growth regulator treatment and one terminal pinch after cuttings were transplanted to the 6-inch pots. Color readings were taken under natural light in the greenhouse. Color references are primarily to the R.H.S. Colour Chart of The Royal Horticultural Society of London (R.H.S.) (2001). Texture description data was viewed with a dissecting microscope.

DETAILED BOTANICAL DESCRIPTION OF THE NEW PLANT

Classification:

*Family.*—Solanaceae.

*Botanical.*—*Calibrachoa* sp.

*Common name.*—*Calibrachoa.*

Parentage:

*Female parent.*—'#33', a proprietary purple-flowered *Calibrachoa* plant (unpatented).

*Male parent.*—'#30', a proprietary deep blue-flowered *Calibrachoa* plant (unpatented).

Growth:

*Form.*—Semi-upright and decumbent (initially spreading to later prostrate and trailing).

*Habit.*—Good vigorous habit, well-branched, full plant; early and continuous flowering response.

*Height* (*measured from the top of the soil*).—8.0 cm to 10.0 cm.

*Width* (*horizontal plant diameter*).—35.0 cm to 40.0 cm.

*Time to produce a finished flowering plant.*—9 to 10 weeks.

*Outdoor plant performance.*—Full sun; free flowering through the summer; used as a hanging plant, in mixed container plantings, mass planting in a bed.

*Time to initiate and develop roots.*—18 to 23 days.

*Root description.*—White, fibrous.

Stems:

*Length of basal branches.*—22.0 cm to 27.0 cm.

*Internode length.*—0.5 cm to 1.0 cm.

*Diameter of branches* (*from midpoint*).—0.15 cm.

*Stem color.*—RHS 144B.

*Texture.*—Glandular hairs of various sizes.

*Anthocyanin.*—Absent.

*Pedicel color.*—RHS 144B.

*Pedicel length.*—0.8 cm to 1.5 cm.

*Pedicel diameter.*—0.1 cm to 0.15 cm.

*Pedicel texture.*—Glandular hairs of various sizes.

Leaves:

*Arrangement.*—Alternate; upper leaves sub-opposite.

*Size.*—Length: 2.3 cm to 2.5 cm. Width: 1.3 cm to 1.5 cm.

*Shape.*—Elliptical.

*Margin.*—Entire.

*Apex.*—Rounded.

*Base.*—Acuminate.

*Color.*—Immature: Upper surface: RHS 137C. Lower surface: RHS 138A. Mature: Upper surface: RHS 137A. Lower surface: RHS 137B.

*Texture.*—Glandular hairs in various sizes.

*Venation.*—Pinnate.

*Venation color.*—RHS 144A, mainly at midrib, otherwise indistinct.

*Petioles.*—Length: 0.2 cm to 0.3 cm. Width: 0.1 cm. Color: RHS 144A. Texture: Glandular hairs in various sizes.

Flower bud:

*Shape.*—Oblong.

*Size.*—Length: 1.5 cm to 2.0 cm. Diameter: 0.5 cm.

*Color at tight bud.*—RHS N77B.

Inflorescence:

*Blooming habit.*—Continuous throughout the growing season; good floriferousness.

*Inflorescence type.*—Flower solitary in upper leaf axis.

*Floret type.*—Funnel form; 5 lobed petals, fused at base.

*Lastingness of individual blooms on the plant.*—5 to 8 days.

*Fragrance.*—Absent.

Flowers:

*Immature flower.*—Diameter: Horizontal: 2.7 cm to 2.9 cm. Vertical: 2.7 cm to 2.8 cm. Color: Upper surface: Velvety, closest to RHS N81A, but darker. Lower surface: Closest to RHS N77B.

*Mature flower.*—Diameter: Horizontal: 3.5 cm to 3.8 cm. Vertical: 3.1 cm to 3.5 cm. Color: Upper surface: Closest to RHS N81A but a little darker and less velvety than the immature flower; fades to between RHS N81A and RHS N81B; a little darker around the corolla opening; RHS N79A veins. Lower surface: RHS N77D.

*Corolla tube.*—Color inside: RHS 8A; RHS 187A at the corolla tube opening. Color outside: RHS 2C with RHS N77C veins. Tube length: 1.5 cm to 1.6 cm. Outside texture: Glandular hairs of various sizes.

*Petals.*—Apex: Emarginate. Base: Fused. Margin: Entire. Waviness of petals: Slight. Lobation: Moderate. Texture: Papillose, with glandular hairs of various sizes on the underside and many on the midveins and at the margins.

*Sepals.*—Calyx: 5 sepals fused at base and somewhat outwardly reflexing. Shape: Lanceolate. Apex: Acute. Base: Fused. Margin: Entire. Length: 1.3 cm to 1.4 cm. Width: 0.3 cm. Color: Upper surface: RHS 138A. Lower surface: RHS 138B. Texture: Glandular hairs of various sizes.

Reproductive organs:

*Stamens.*—Number: 5, 2 long, 3 short. Filament color: Closest to but lighter than RHS 150C. Filament length: 0.7 cm to 0.9 cm. Filament diameter: Less than 0.1 cm. Pollen color: RHS 9C. Pollen quantity: Moderate.

*Pistils.*—Number: 1. Length: 0.9 cm to 1.0 cm. Diameter: Less than 0.1 cm. Stigma color: RHS 143B. Style color: RHS 150C.

Fruit and seed set: No seed set observed.

Disease and insect resistance: No particular resistance or susceptibility has been observed.

COMPARISON WITH PARENTAL AND COMMERCIAL CULTIVARS

'Cal Pur07' differs from the female parent '#33' (unpatented) by having darker green leaves than '#33'. Additionally, 'Cal Pur07' is more floriferous and has a more prostrate growth habit than '#33'.

'Cal Pur07' differs from the male parent '#30' (unpatented) by having smaller leaves and shorter internodes than '#30'. Additionally, 'Cal Pur07' is earlier to flower than '#30'.

'Cal Pur07' differs from the commercial cultivar 'Cal Pur' (U.S. Plant Pat. No. 15,427) by having more intense flower color with less fading than 'Cal Pur'. Additionally, 'Cal Pur07' has narrower and darker green foliage than 'Cal Pur'.

I claim:

1. A new and distinct cultivar of *Calibrachoa* plant as shown and described herein.

* * * * *